United States Patent
Blake et al.

(10) Patent No.: US 6,601,275 B2
(45) Date of Patent: Aug. 5, 2003

(54) METHOD AND COMPOSITION FOR EMBALMING

(75) Inventors: Wayne Clayton Blake, Wallingford, CT (US); Richard Anthony Simonelli, North Haven, CT (US)

(73) Assignee: United Biotechnologies, L.L.C., Hamden, CT (US)

( * ) Notice: Subject to any disclaimer, the term of this patent is extended or adjusted under 35 U.S.C. 154(b) by 94 days.

(21) Appl. No.: 09/790,958

(22) Filed: Feb. 22, 2001

(65) Prior Publication Data

US 2001/0032381 A1 Oct. 25, 2001

Related U.S. Application Data

(60) Provisional application No. 60/183,888, filed on Feb. 22, 2000.

(51) Int. Cl.⁷ ................................................. A01N 1/00
(52) U.S. Cl. ....................................................... 27/22.2
(58) Field of Search .................................. 27/22.1, 22.2

(56) References Cited

U.S. PATENT DOCUMENTS 4,416,909 A  * 11/1983 Aversano

* cited by examiner

*Primary Examiner*—Dennis Ruhl
(74) *Attorney, Agent, or Firm*—John J. Daniels, Esq.

(57) ABSTRACT

A method for and a preservative composition for use in embalming a dead human body to temporarily maintain a desirable state of non-decomposition. The method comprising the steps of draining blood from the circulatory system of a dead body; and injecting a preservative composition into the drained circulatory system of the dead human body. The preservative composition consisting essentially of from 10 to 40% of each of the following components: a material selected from the group consisting of ascorbic acid, the sodium and potassium salts thereof and mixtures thereof; a material selected form the group consisting of citric acid, the sodium and potassium salts thereof and mixtures thereof; a material selected from the group consisting of sodium carbonate, potassium carbonate and mixtures thereof; and material selected from the group consisting of sodium and potassium sulfite, bisulfite, and metabisulfite and mixtures thereof. The inventive preservative composition may further include skin treatment components including lanolin, carboxymethylcellulose, methymethacrylate gel, humectants, and hydrolyzed proteins.

5 Claims, No Drawings

METHOD AND COMPOSITION FOR EMBALMING

This application claims benefit of Provisional Application Ser. No. 60/183 888 filed Feb. 22, 2000.

BACKGROUND OF THE INVENTION

The present invention pertains to the field of preservation of human tissue in the field of mortuary science. More particularly, the present invention pertains to a method and preservative composition for embalming a dead body using an enviromentally safe, formaldehyde-free embalming composition.

Arterial embalming, as a mortuary practice, is considered to have begun in England in the 18th century. William Hunter (1718–1783) is credited as the first person to embalm a body for burial preparation. His younger brother John Hunter achieved notoriety by embalming the body of Mrs. Martin Van Butchell, whose will specified her widower spouse had control of her estate only as long as her body remained above ground. To meet the condition, Mr. Van Butchell placed his wife's embalmed body in a glass-lidded case and held regular sitting hours.

The demand for embalming grew in England and particularly in the United States, where it was promoted by the emergent undertaking business as a superior alternative for the preservation of bodies for transportation. Traditionally, bodies were preserved by packing them in ice and laying them on cooling boards.

The United States Civil War marked a turning point for the use of arterial embalming due to the widespread use of embalming the bodies of fallen soldiers prior to transportation to the newly established national war cemeteries. This brought about increased acceptance to the practice.

Modern embalming practice begins with controlled disaffection of the entire body. If the body is not saturated with the sufficient level of germicidal arterial fluid, it may become the medium for the microbial growth of pathogens. In the conventional practice of embalming, the blood is drained from the circulatory system and replaced by an embalming fluid, usually based on Formalin, (a solution of formaldehyde and water), by injecting the embalming fluid into one of the main arteries.

Formaldehyde is a basic ingredient of a conventional embalming fluid. The fluid may bleach or flush a corpse, so dyes may be added to redden or tan the body to give a more life-like appearance. Also, an emollient may be added to keep the skin soft. Once the embalming fluid is in the body, most of it becomes a gas and dries the proteins in the body.

An example of a conventional cervical-injection embalming method begins with the insertion of a drain tube in the jugular vein and a short arterial tube into the carotid artery. Continuous injection and drainage of a formaldehyde-based embalming fluid is the most common method in use today, although this method may be dangerous to both the operator and environment. Continuous injection and drainage allow the arterial fluid to follow the course of least resistance as it is pumped through the circulatory system. However, this conventional embalming method is known to expose the operator, as well as the environment, to high levels of formaldehyde.

Studies indicate that formaldehyde is a potential human carcinogen. Airborne concentrations above 0.1 parts per million (ppm) can cause irritation of the eyes nose and throat. The severity of irritation increases as concentrations increase; at 100 ppm it is immediately dangerous to life and health.

The permissible exposure limit (PEL) for formaldehyde in all workplaces (including general industry, construction, and maritime, but not in agriculture) covered by the Occupational Safety and Health Administration (OSHA) Act (29 CRF 1919.1048) is 0.75 ppm measured as an 8-hour time weighted Average (TWA). The standard includes a 2 ppm short-term exposure limit (STEL) (i.e., maximum exposure allowed during a 15-minute period). The "action level" is 0.5 ppm measured over 8 hours (see, OSHA Fact Sheet No. 95–27, Jan. 1, 1995—*Occupational Exposure to Formaldehyde*).

However, even with careful practice embalmers are often subjected to high doses of formaldehyde during the embalming process. It has been determined that embalmers are exposed to formaldehyde at concentrations averaging up to 9 ppm during embalming, significantly above the OSHA STEL limitation of 2 ppm (see, NIOSH *Hazard Control 26/Controlling Formaldehyde Exposure During Embalming*).

There have been attempts to provide a formaldehyde-free embalming compositions. U.S. Pat. No. 3,983,252 to Buchalter, discloses a stable dialdehyde-containing disinfectant for use in the medical field and household objects. The compositions described in this patent are also disclosed to be useful in leather tanning, tissue fixation for electric microscopy, protein reactions and embalming fluids. U.S. Pat. No. 5,948,397 to Van Kersen, et al., discloses skin care treatment for embalmed bodies. The goal of the composition disclosed in this patent is to prevent skin protein denaturing and desiccation of skin due to the process of embalming. U.S. Pat. No. 5,679,333 to Dunphy, discloses a formaldehyde free tissue preservative compositions useful in the field of mortuary science and histology. Disclosed in this patent are compositions of an aqueous solution ethanol, ethanedial, a long polymer and polar aprotic solvents as an arterial injection fluid for use in preserving animal bodies. Also disclosed is a formaldehyde-free composition of aqueous solutions of ethanedial, a polar aprotic solvent, a proteolytic enzyme, a surfactant, an anti-microbial agent and optionally, a chelating agent as a pre-injection composition to cleanse the circulatory in preparation for the administration of the inventive tissue preservative composition. In addition, this patent describes a formaldehyde-free body cavity fluid for the use in the embalming process, which comprises an aqueous solution of ethanol, an organic compound, a polar aprotic solvent, ethanedial and Bisphenol A. U.S. Pat. No. 4,675,327 to Fredrick, discloses antimicrobial compositions for embalming preparations comprising a combination of a disinfectant and a plant growth regulating compound. Disclosed as disinfectants are a wide variety of anti bacterial agents such as sulfonamides, penicillin, cephalosporin, and bactracin, etc., and salts thereof. Anti-fungal agents disclosed include, griseofulvin, nystatin, etc., and salts thereof. Disclosed as skin disinfectants are alcohols, sources of active halogens, phenolics and their derivatives, salts such as sodium hypochloride, aldehydes including formaldehyde, peracids and their derivatives, quaternary ammonium compounds. Disclosed as metal binding agents include chelating compounds and sequestering compounds, and numerous dyes. Other disinfectants disclosed are heavy metal disinfectants such as mercurial compounds, copper compounds, silver compounds, and arsenic compounds. These prior attempts disclose various compositions of a formaldahyde-free embalming fluid. However, each of these attempts has certain drawbacks in terms of factors such as cost of components, health or enviromental hazards of the components, ineffectiveness at preventing decomposition and the like.

SUMMARY OF THE INVENTION

It is an object of the present invention to provide a composition for an embalming fluid which is effective for temporarily preventing the decomposition of a dead body, helps to maintain a desired life-like appearance of the body, is non-hazardous to embalmers, is environmentally benign during the embalming process, and remains environmentally benign as the body decomposes over time.

In accordance with the present invention, a method is provided for embalming a dead body to temporarily maintain a desirable state of non-decomposition. The inventive method comprises the steps of (1) draining blood from the circulatory system of a dead body; and (2) injecting the inventive preservative composition into the drained circulatory system of the dead body.

The inventive preservative composition consists essentially of from 10 to 40% of each of the following components:

(a) a material selected from the group consisting of ascorbic acid, the sodium and potassium salts thereof and mixtures thereof;

(b) a material selected form the group consisting of citric acid, the sodium and potassium salts thereof and mixtures thereof;

(c) a material selected from the group consisting of sodium carbonate, potassium carbonate and mixtures thereof; and (d) a material selected from the group consisting of sodium and potassium sulfite, bisulite, and metabisulfate and mixtures thereof.

The inventive preservative composition may also include a skin treatment component The skin treatment component includes at least one of lanolin, carboxymethylcellulose, methymethacrylate gel, humectants, hydrolyzed proteins and a liquid crystalline carrier.

DETAILED DESCRIPTION OF THE INVENTION

The composition of the present invention may be effectively used in preserving animal (including, but not limited to, human) tissue. Preservation can be achieved by arterial injection of the inventive composition (commonly referred to as embalming) or by the submergence in an aqueous solution of the inventive composition (as for laboratory specimen preparation).

In the field of mortuary science, the skin of the deceased may be treated by dusting the exposed surfaces with the inventive composition or by spraying with an aqueous solution thereof (in order to maintain skin color). Addition of an emollient, such as lanolin, to the inventive composition spray may be employed to maintain skin suppleness.

In accordance with the present invention, ascorbic acid component may be ascorbic acid itself and/or the sodium and/or potassium salts thereof. Similarly, citric acid component may be citric acid itself and/or the sodium and/or potassium salts thereof (i.e., sodium or potassium citrate).

Either sodium and/or potassium carbonate can be employed. The sulfite component may be sulfite, bisulfite and/or metabisulfite of sodium and/or potassium.

Additionally, tissue and color preservation may be enhanced by adding nitrates or nitrites phosphates, nicotinic acid or other known color or freshness preservatives. The synergistic combination of the components has been shown to effectively maintain the non-decomposition of animal tissue for an inordinately long period of time without the reliance of formaldehyde-based compounds.

As described in U.S. Pat. No. 4,416,909 to Aversano, issued Nov. 22, 1983, and incorporated by reference within, experimental data supports the effectiveness of the inventive composition as a preservative of animal tissue, and as a color maintenance agent. Additional experimentally obtained data confirmed the inventive composition's effectiveness as a *Escherchia coli* bacteriostic (growth inhibiting) agent and concluded the composition did prevent growth of the organism even at one forth of the patented concentration.

Accrodingly, the present invention makes use of the composition described in the above-referenced Aversano patent for the purpose of embalming a dead body.

In accordance with the present invention, a method is provided for embalming a dead body to temporarily maintain a desirable state of non-decomposition. The inventive method comprises the steps of (1) draining blood from the circulatory system of a dead body; and (2) injecting the inventive preservative composition into the drained circulatory system of the dead body.

The inventive preservative composition is a substance that has been experimentally determined to be effective at preventing the growth of bacteria and prevent the decay and discoloration of beef. In accordance with the present invention, this composition is employed as an embalming medium for use in temporarily maintaining a desired state of non-decomposition of a dead human body.

The inventive preservative composition consists essentially of from 10 to 40% of each of the following components:

(a) a material selected from the group consisting of ascorbic acid, the sodium and potassium salts thereof and mixtures thereof;

(b) a material selected form the group consisting of citric acid, the sodium and potassium salts thereof and mixtures thereof;

(c) a material selected from the group consisting of sodium carbonate, potassium carbonate and mixtures thereof, and (d) a material selected from the group consisting of sodium and potassium sulfite, bisulfite, and metabisulfate and mixtures thereof.

In accordance with one embodiment of the inventive method and the inventive preservative composition the components of the inventive preservative composition are present in substantially equal quantities.

In accordance with another embodiment of the inventive method and the inventive preservative composition the components of the inventive preservative composition are ascorbic acid, citric acid, sodium carbonate and sodium bisulfate.

In accordance with another embodiment of the inventive method and the inventive preservative composition the preservative composition further consists of a skin treatment component, and the skin treatment component comprises at least one of lanolin, carboxymethylcellulose, methymethacrylate gel, humectants, hydrolyzed proteins and a liquid crystalline carrier.

In accordance with the present invention, a method and preservative composition is provided which effectively temporarily reduce or prevent the decomposition of a dead human body, while maintaining a life-like look of the skin of the body. The inventive preservative composition is based on materials which are safely handled and which are environmentally benign.

What is claimed is:

1. A method for embalming a dead human body to temporarily maintain a desirable state of non-decomposition, comprising the steps of: draining blood from the circulatory system of a dead human body; injecting a preservative composition into the drained circulatory system of the dead human body, the preservative composition comprising of from 10 to 40% of each of the following components:

(e) a material selected from the group consisting of ascorbic acid, the sodium and potassium salts thereof and mixtures thereof;

(f) a material selected form the group consisting of citric acid, the sodium and potassium salts thereof and mixtures thereof;

(g) a material selected from the group consisting of sodium carbonate, potassium carbonate and mixtures thereof; and (h) a material selected from the group consisting of sodium and potassium sulfite, bisulfite, and metabisulfite and mixtures thereof.

2. A method according to claim 1 wherein said components are present in substantially equal quantities.

3. A method according to claim 1 wherein said components are ascorbic acid, citric acid, sodium carbonate and sodium bisulfate.

4. A method according to claim 1 wherein said preservative composition further comprises a skin treatment component.

5. A method according to claim 4 wherein said skin treatment component comprises at least one of lanolin, carboxymethylcellulose, methymethacrylate gel, humectants, and hydrolyzed proteins.

* * * * *